United States Patent [19]
Ciszewski et al.

[11] Patent Number: 5,608,061
[45] Date of Patent: Mar. 4, 1997

[54] PROCESS FOR PREPARING 1,4,8,11-TETRAAZACYCLOTETRADECANE

[75] Inventors: Lech Ciszewski, Morristown, N.J.; John Amedio, Franklin, Mass.; Prasad Kapa, Parsippany, N.J.; Andrew Kucerovy, Flanders, N.J.; George T. Lee, Bloomfield, N.J.

[73] Assignee: Johnson Matthey PLC, London, England

[21] Appl. No.: 510,207

[22] Filed: Aug. 2, 1995

[51] Int. Cl.$^6$ ............................................. C07D 255/02
[52] U.S. Cl. ........................ 540/474; 540/450; 540/470
[58] Field of Search ............................................. 540/474

[56] References Cited

U.S. PATENT DOCUMENTS

| | | | |
|---|---|---|---|
| 5,021,409 | 6/1991 | Murrer et al. | 540/474 |
| 5,047,527 | 9/1991 | Handel et al. | 540/474 |
| 5,284,944 | 2/1994 | Madison et al. | 540/474 |
| 5,386,028 | 1/1995 | Tilstam et al. | 540/474 |

FOREIGN PATENT DOCUMENTS

| | | |
|---|---|---|
| 374929 | 6/1990 | European Pat. Off. . |
| 9312096 | 6/1993 | WIPO . |

OTHER PUBLICATIONS

J. Med. Chem., vol. 38, No. 2, pp. 366–378 (1995).

Primary Examiner—Mukund J. Shah
Assistant Examiner—Pavanaram K. Sripada
Attorney, Agent, or Firm—Cushman Darby & Cushman IP Group Pillsbury Madison & Sutro LLP

[57] ABSTRACT

An improved process for preparing 1,4,8,11-tetraazacyclotetradecane comprising the tetratosylation of an acyclic tetraamine to obtain a tetratoluenesulfonamide compound in a first step, the cyclization of said sulfonamide compound to obtain tetratosyl cyclam in a second step, and the detosylation of tetratosyl cyclam in a third step followed by basification to obtain the desired 1,4,8,11-tetraazacyclotetradecane.

20 Claims, No Drawings

PROCESS FOR PREPARING 1,4,8,11-TETRAAZACYCLOTETRADECANE

BACKGROUND OF THE INVENTION

1. Field of the Invention

The present invention relates to the area of cyclic tetraamines and, more particularly, relates to an improved process for preparing a specific cyclic tetraamine which is a valuable starting material in the preparation of a specific pharmaceutically active 1,4-phenylenebis-(methylene)-linked cyclam dimer.

2. Description of the Prior Art

U.S. Pat. No. 5,021,409 is directed to a method of treating retroviral infections comprising administering to a mammal in need of such treatment a therapeutically effective amount of a bicyclic macrocyclic polyamine compound. Although the usefulness of certain alkylene and arylene bridged cyclam dimers is generically embraced by the teachings of the reference, no arylene bridged cyclam dimers are specifically disclosed. In addition, although no specific processes are set forth for preparing the alkylene and arylene bridged cyclam dimers, it is believed that at least some of them are prepared employing 1,4,8,11-tetraazacyclotetradecane (aka. cyclam) as the starting material.

WO 93/12096 discloses the usefulness of certain linked cyclic polyamines in combating HIV and pharmaceutical compositions useful therefor. Among the specifically disclosed compounds is 1,1'-[1,4-phenylenebis-(methylene)]-bis-1,4,8,11-tetraazacyclotetradecane (and its acid addition salts), which compound is a highly potent inhibitor of several strains of human immune deficiency virus type 1 (HIV-1) and type 2 (HIV-2). Although no specific processes are set forth for preparing said compound, it is believed to be prepared employing 1,4,8,11-tetraazacyclotetradecane as the starting material.

European Patent Appln. 374,929 discloses a process for preparing mono-N-alkylated polyazamacrocycles comprising reacting the unprotected macrocycle with an electrophile in a non-polar, relatively aprotic solvent in the absence of base. Although one of the specifically disclosed macrocycles is 1,4,8,11-tetraazacyclotetradecane, it is indicated 1to have been purchased commercially from Aldrich Chemical Co.

U.S. Pat. No. 5,047,527 is directed to a process for preparing a monofunctionalized (e.g., monoalkylated)cyclic tetraamine comprising: 1) reacting the unprotected macrocycle with chromium hexacarbonyl to obtain a triprotected tetraazacycloalkane compound; 2) reacting the free amine group of the triprotected compound prepared in 1) with an organic (e.g., alkyl) halide to obtain a triprotected monofunctionalized (e.g., monoalkylated) tetraazacycloalkane compound; and 3) de-protecting the compound prepared in 2) by simple air oxidation at acid pH to obtain the desired compound. In addition, the reference discloses alterative methods of triprotection employing boron and phosphorous derivatives and the preparation of linked compounds, including the cyclam dimer 1,1'-[1,4-phenylenebis-(methylene)]-bis-1,4,8,11-tetraazacyclotetradecane, by reacting triprotected cyclam prepared as set forth in 1) above with an organic dihalide in a molar ratio of 2:1, and deprotecting the resultant compound to obtain the desired cyclam dimer. Although one of the specifically disclosed macrocycles is cyclam, since no mention is made regarding its method of preparation, it is believed to have been obtained commercially.

J. Med. Chem., Vol. 38, No. 2, pgs. 366–378 (1995) is directed to the synthesis and anti-HIV activity of a series of novel phenylenebis(methylene)-linked bis-tetraazamacrocyclic analogs, including the known cyclam dimer 1,1'-[1,4-phenylenebis(methylene)]-bis-1,4,8,11-tetraazacyclotetradecane. The cyclam dimers disclosed in this reference, including the afore-mentioned cyclam dimer, are prepared by: 1) forming the tritosylate of the tetraazamacrocycle; 2) reacting the protected tetraazamacrocycle with an organic dihalide, e.g., dibromo-p-xylene, in acetonitrile in the presence of a base such as potassium carbonate; and 3) de-protecting the bis-tetraazamacrocycle prepared in 2) employing fleshly prepared sodium amalgam, concentrated sulfuric acid or an acetic acid/hydrobromic acid mixture to obtain the desired cyclam dimer, or an acid addition salt thereof. Although one of the specifically disclosed macrocycles is cyclam, it is indicated to have been obtained commercially.

From the above, it is clear that the compound 1,4,8,11-tetraazacyclotetradecane (aka. cyclam) is a valuable starting material in the preparation of a number of pharmacologically active compounds, including the highly potent anti-HIV compound 1,1'-[1,4-phenylenebis-(methylene)]-bis-1,4,8,11-tetraazacyclotetradecane. However, since cyclam is expensive and not readily available, there was a need to develop a more practical process for preparing 1,4,8,11-tetraazacyclotetradecane.

SUMMARY OF THE INVENTION

The present invention relates to a more efficient and economic process for preparing 1,4,8,11-tetraazacyclotetradecane employing an inexpensive and readily available acyclic tetraamine compound as the starting material. More particularly, the present invention involves the tetratosylation of an acyclic tetraamine to obtain a tetratoluenesulfonamide compound in a first step, the cyclization of said sulfonamide compound to obtain tetratosyl cyclam in a second step, and the detosylation of tetratosyl cyclam in a third step followed by basification to obtain the desired 1,4,8,11-tetraazacyclotetradecane.

DETAILED DESCRIPTION OF THE INVENTION

The present invention relates to an improved process for preparing 1,4,8,11-tetraazacyclotetradecane. More particularly, said compound is prepared by a three-step process as depicted below:

STEP 1

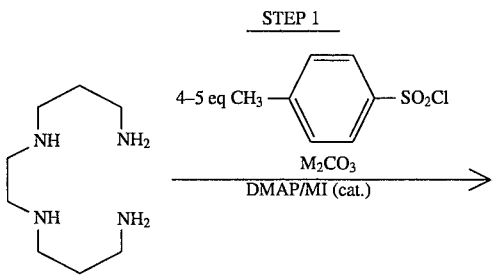

3
-continued
STEP 1

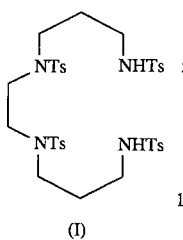

where M is an alkali metal.

STEP 2

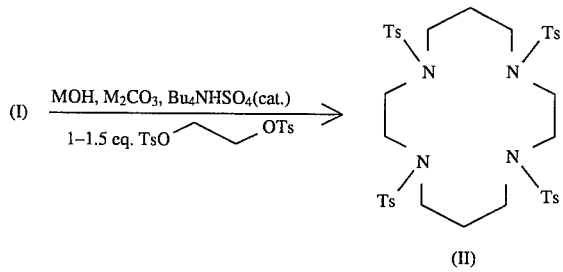

where M is as defined above.

STEP 3

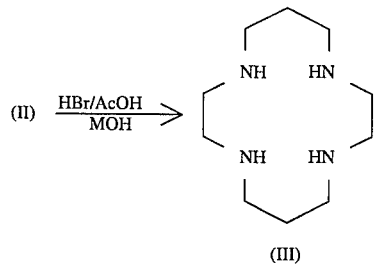

where M is as defined above.

With respect to the individual steps, Step 1 involves the reaction of N,N'-bis(3-aminopropyl)ethylenediamine with 4 to 5 equivalents of p-toluenesulfonylchloride in the presence of an alkali metal carbonate such as sodium carbonate and a catalytic amount of a mixture of 4-dimethylaminopyridine (DMAP) and an alkali metal iodide such as sodium iodide to yield the tetratoluenesulfonamide compound of formula I. The tetratosylation reaction is carried out in the presence of a cyclic ether such as tetrahydrofuran at a temperature of from 55° to 75° C. for a period of between 3 and 5 hours.

Step 2 concerns the cyclization of the compound prepared in Step 1, i.e., the sulfonamide compound of formula I, by reacting it with 1 to 1.5 equivalents of ethyleneglycol ditosylate in the presence of a mixture of an alkali metal hydroxide such as sodium hydroxide (in bead form) and an alkali metal carbonate such as potassium carbonate (in anhydrous form) and a catalytic amount of tetrabutylammonium hydrogen sulfate to obtain tetratosyl cyclam of formula II. The cyclization is carried out in the presence of dimethylformamide at a temperature of from 75° C. to 125° C. for a period of between 4 and 7 hours.

Alternatively, the sulfonamide compound of formula I can be reacted with 1 to 1.5 equivalents of ethyleneglycol ditosylate in the presence of cesium carbonate in dimethylformamide at a temperature of from 75° C. to 125° C. for a period of between 4 and 7 hours to obtain tetratosyl cyclam of formula II.

Step 3 involves the detosylation of the compound prepared in Step 2, i.e., tetratosyl cyclam of formula II, by reacting it with a mixture of hydrobromic acid (48% solution) and glacial acetic acid. The product is then basified with an alkali metal hydroxide solution (e.g., a 50% sodium hydroxide solution) to obtain the desired compound of formula III. The detosylation is carried out at reflux temperature for a period of between 30 hours and 3 days. Alternatively, the detosylation may be carried out by reacting the compound prepared in Step 2 with concentrated sulfuric acid or with a mixture of sodium phosphate and freshly prepared sodium amalgam in an argon atmosphere. The detosylation with concentrated sulfuric acid may be carried out at a temperature of from 80° C. to 120° C. for a period of between 2 and 5 may be carried out at a temperature of from 80° C. to 120° C. for a period of between 2 and 5 hours, whereas the detosylation with a mixture of sodium phosphate and sodium amalgam may be carried out at a temperature of from 80° C. for a period of between 1 and 4 days.

As alluded to above, the acyclic tetraamine compound employed as the starting material in Step 1 is known and commercially available.

Although the crude product of one reaction may be employed in the following reaction without purification, it has been found highly desirable to purify the product of each reaction described above in Steps 1 and 2 by conventional techniques such as recrystallization (if a solid).

The following example is for purposes of illustration only and is not intended to limit in any way the scope of the instant invention.

EXAMPLE a) Preparation of the Tetratoluenesulfonamide Compound of Formula I

To a 12-L, 4-necked, round-bottom flask, equipped with a mechanical stirrer, heating mantle, internal thermometer, addition funnel and refluxing condenser, and which has been purged with nitrogen, is added 303 ml. (1.602 mol) of N,N'-bis(3-aminopropyl)ethylenediamine, 711 g. (6.708 mol) of anhydrous sodium carbonate, 1.2 g. (0.008 mol) of sodium iodide, 1.0 g. (0.0082 mol) of 4-dimethylaminopyridine and 6.384 L. of water, and the resultant mixture is stirred at a temperature between 40° C. and 45° C. for 5 minutes. The mixture is then heated to 62° C. and to the heated mixture is slowly added, over a period of 60 minutes, a solution of 1.353 kg. (6.957 mol) of p-toluenesulfonyl chloride in 1.92 L. of tetrahydrofuran, while the temperature is maintained at between 63° C. and 65° C. After the addition funnel is rinsed with 100 ml. of tetrahydrofuran, the reaction mixture is allowed to reflux at a temperature between 64° C. and 66° C. for 2 hours. The reaction mixture is then allowed to cool slightly to a temperature between 55° C. and 57° C. and the two layers are allowed to settle over a period of between 5 and 10 minutes. The bottom aqueous layer is then extracted with a mixture of 100 ml. of heptane and 100 ml. of tetrahydrofuran at a temperature between 55° C. and 56° C. The bottom aqueous layer is then discarded and the heptane/tetrahydrofuran extract is transferred to the other layer. A solution of 15 ml. of concentrated hydrochloric acid in 350 ml. of water is then added at a temperature between 45° C. and 55° C. and the mixture is stirred for 5 minutes. 1.34 L. of heptane is then added over a period of 2 minutes while the temperature is maintained between 40° C. and 45° C. The mixture is then cooled to. 22° C. over a period of 30 minutes to obtain an off-white suspension which is filtered. The filter cake is then washed with two 500 ml. portions of water and sucked under house vacuum for 1 hour. The filter cake is then washed with 250 ml. of anhydrous ethanol and transferred to the previous 12-L, round-bottom flask. 3 L. of anhydrous ethanol is then added, the suspension is heated to 75° C. over 30 minutes and slurried while refluxing for 5 minutes. The suspension is then cooled to 25° C., filtered and the filter cake is washed with 500 ml. of anhydrous ethanol. The filter cake is then dried in a vacuum oven at a temperature of between 75° C. and 80° C. for 2 days to yield the desired compound as a white solid.

b) Preparation of Tetratosyl Cyclam of Formula II

To a 5-L, 4-necked, round-bottom flask, equipped with a mechanical stirrer, heating mantle, internal thermometer, addition funnel and reflux condenser, and which has been purged with nitrogen, is added 1.4 L. of dimethylformamide, 79.0 g. (0.099 mol) of the sulfonamide compound prepared in a) above, 14.0 g. (0.35 mol) of sodium hydroxide beads and 16.5 g. (0.119 mol) of anhydrous potassium carbonate. The resultant faint yellow suspension is heated to 80° C. and maintained at this temperature, with stirring, for 3 hours. To the heated mixture is then added 3.4 g. (0.010 mol) of tetrabutylammonium hydrogen sulfate, and the resultant mixture is warmed to 100° C. over a period of 20 minutes. To this heated mixture is then added dropwise, over a period of 2 hours, a solution of 55.6 g. (0.138 mol) of ethyleneglycol ditosylate in 1 L. of dimethylformamide, while the temperature is maintained at 100° C. The resultant tan mixture is then stirred at 100° C. for 2 hours, after which time it is cooled to a temperature between 20° C. and 25° C. and stirred for an additional 16 hours. The mixture is then cooled to a temperature between 0° C. and 5° C. and quenched by the addition of 2 L. of water over a period of 20 minutes. The temperature of the mixture is then allowed to warm to 25° C. and the resultant suspension is stirred at 25° C. for 2 hours. The suspension is then vacuum filtered and the filtered material is rinsed with 500 ml. of water. The filtrate/washing is then discarded and the damp filter cake is transferred to a 1-L, 4-necked, round-bottom flask, equipped with a mechanical stirrer, heating mantle, internal thermometer, addition funnel and reflux condenser and to which has been added 250 ml. of acetonitrile. The resultant suspension is then heated at a temperature between 78° C. and 79° C. for 30 minutes, cooled to 25° C. and stirred for 1 hour. The mixture is then vacuum filtered and rinsed with 150 ml. of acetonitrile. The filter cake is then dried in a vacuum oven at a temperature of 85° C. for 18 hours to yield the desired compound as a white/off-white solid.

c) Preparation of 1,4,8,11-tetraazacyclotetradecane

To a 12-L, 4-necked, round-bottom flask, equipped with a mechanical stirrer, heating mantle, internal thermometer, addition funnel and reflux condenser, is added 200 g. (0.245 mol) of tetratosyl cyclam prepared in b) above, 1.8 L. of 48% hydrobromic acid and 3.3 L. of glacial acetic acid. The resultant mixture is then heated to reflux and maintained at reflux temperature, with stirring, for 42 hours. The reaction mixture is then cooled to between 22° C. and 23° C. over a period of 4 hours, after which time it is stirred for an additional 12 hours. The solids are then collected using suction filtration and added to 800 ml. of deionized water. The resultant solution is then stirred for 25 to 30 minutes at a temperature between 22° C. and 23° C. and cooled to a temperature between 0° C. and 5° C. To the cooled solution is then added, over a period of 30 minutes, 264 g. of sodium hydroxide dissolved in 264 ml. of deionized water, while the temperature is maintained at between 5° C. and 15° C. The resultant suspension is then cooled to a temperature between 0° C. and 5° C. and stirred at this temperature for between 10 and 15 minutes. The suspension is then warmed to between 22° C. and 23° C. and filtered using suction filtration. The solids collected are then washed with two 160 ml. portions of acetone and dried in a vacuum oven at a temperature between 85° C. and 90° C. for 15 hours. The dry solids are then added to 700 ml. of 2-propanol, the mixture is stirred vigorously and then filtered using suction filtration. The filter is then washed with 100 ml. of 2-propanol, and the filtrate is concentrated under reduced pressure (40°–45° C. bath temperature, 70–75 mm. Hg) until approximately 700 ml. of solvent is collected. To the resultant slurry is then added 700 ml. of toluene, and the filtrate is concentrated under reduced pressure (40°–45° C. bath temperature, 70–75 mm. Hg) until approximately 700 ml. of solvent is collected. To this slurry is then added 700 ml. of toluene, and the filtrate is concentrated under reduced pressure (40°–45° C. bath temperature, 70–75 mm. Hg) until approximately 600 ml. of solvent is collected. This slurry is then cooled to between 22° C. and 23° C. and filtered using suction filtration. The solids collected are then washed with three 200 ml. portions of acetone and dried in a vacuum oven at a temperature between 50° C. and 60° C. for 15 hours to obtain the desired compound.

What is claimed is:

1. A process for preparing 1,4,8,11-tetraazacyclotetradecane comprising the steps of:

1) tetratosylating an acyclic tetraamine in a first step;

2) cyclizing the tetratoluenesulfonamide compound prepared in the first step; and 3) detosylating the tetratosyl cyclam compound prepared in the second step.

2. A process according to claim 1 comprising the steps of:

1) reacting N,N'-bis(3-aminopropyl)ethylene diamine with 4 to 5 equivalents of p-toluenesulfonylchloride to obtain the tetratoluenesulfonamide compound of formula I

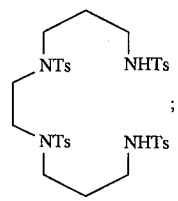

2) cyclizing the sulfonamide compound prepared in the first step by reacting it with 1 to 1.5 equivalents of ethyleneglycol ditosylate to obtain the tetratosyl cyclam compound of formula II

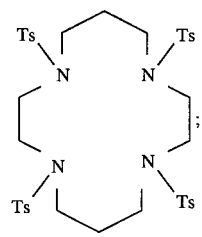

3) detosylating the tetratosyl cyclam compound prepared in the second step and basifying the reaction mixture to obtain 1,4,8,11-tetraazacyclotetradecane of formula III

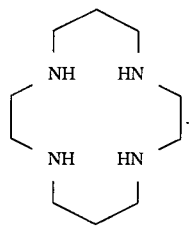

3. A process according to claim 2 wherein the tetratosylation reaction of the first step is carried out in the presence of an alkali metal carbonate and a catalytic amount of a mixture of 4-dimethylaminopyridine and an alkali metal iodide.

4. A process according to claim 3 wherein the reaction is carried out in the presence of sodium carbonate and a catalytic amount of a mixture of 4-dimethylaminopyridine and sodium iodide.

5. A process according to claim 3 wherein the reaction is carried out in the presence of a cyclic ether at a temperature of from 55° C. to 75° C. for a period of between 3 and 5 hours.

6. A process according to claim 5 wherein the reaction is carried out in the presence of tetrahydrofuran at a temperature of from 55° C. to 75° C. for a period of between 3 and 5 hours.

7. A process according to claim 2 wherein the cyclization reaction is carried out in the presence of a mixture of an alkali metal hydroxide and an alkali metal carbonate and a catalytic amount of tetrabutylammonium hydrogen sulfate.

8. A process according to claim 7 wherein the reaction is carried out in the presence of a mixture of sodium hydroxide and potassium carbonate and a catalytic amount of tetrabutylammonium hydrogen sulfate.

9. A process according to claim 7 wherein the reaction is carried out in the presence of dimethylformamide at a temperature of from 75° C. to 125° C. or a period of between 4 and 7 hours.

10. A process according to claim 2 wherein the cyclization reaction is carried out in the presence of cesium carbonate.

11. A process according to claim 10 wherein the reaction is carried out in the presence of dimethylformamide at a temperature of from 75° C. to 125° C. for a period of between 4 and 7 hours.

12. A process according to claim 2 wherein the detosylation reaction is carried out with a mixture of hydrobromic acid and glacial acetic acid.

13. A process according to claim 12 wherein the reaction is carried out at reflux temperature for a period of between 30 hours and 3 days.

14. A process according to claim 2 wherein the basification in the third step is carried out with an alkali metal hydroxide.

15. A process according to claim 14 wherein the basification is carried out with sodium hydroxide.

16. A process according to claim 2 wherein the detosylation reaction is carried out with concentrated sulfuric acid.

17. A process according to claim 16 wherein the reaction is carried out at a temperature of from 80° C. to 120° C. for a period of between 2 and 5 hours.

18. A process according to claim 2 wherein the detosylation reaction is carried out with a mixture of sodium phosphate and freshly prepared sodium amalgam in an argon atmosphere.

19. A process according to claim 18 wherein the reaction is carried out at a temperature of from 80° C. to 120° C. for a period of between 1 and 4 days.

20. A process for preparing 1,4,8,11-tetraazacyclotetradecane comprising the steps of:

1) reacting N,N'-bis(3-aminopropyl)ethylene diamine with 4 to 5 equivalents of p-toluenesulfonylchloride in the presence of an alkali metal carbonate, a catalytic amount of a mixture of 4-dimethylaminopyridine and an alkali metal iodide, and a cyclic ether at a temperature of from 55° C. to 75° C. for a period of between 3 and 5 hours to obtain the tetratoluenesulfonamide compound of formula I

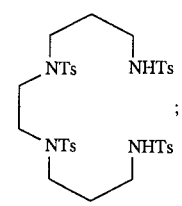

2) cyclizing the sulfonamide compound prepared in the first step by reacting it with 1 to 1.5 equivalents of ethyleneglycol ditosylate in the presence of a mixture of an alkali metal hydroxide and an alkali metal carbonate, a catalytic amount of tetrabutylammonium hydrogen sulfate and dimethylformamide at a temperature of from 75° C. to 125° C. for a period of between 4 and 7 hours to obtain the tetratosyl cyclam compound of formula II

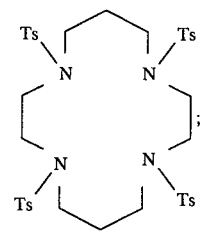

3) detosylating the tetratosyl cyclam compound prepared in the second step by reacting it with a mixture of hydrobromic acid and glacial acetic acid at reflux temperature for a period of between 30 hours and 3 days and then basifying the reaction mixture with an alkali metal hydroxide to obtain 1,4,8,11-tetraazacyclotetradecane of formula III

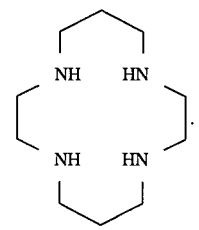

* * * * *